United States Patent
Brandt et al.

[11] Patent Number: 5,762,651
[45] Date of Patent: Jun. 9, 1998

[54] DUSTPROOFING AGENTS

[75] Inventors: Horst Brandt, Odenthal; Hans Schulze, Köln; Thomas Nagel, Bergisch Gladbach; Hans-Werner Petroll, Kürten; Udo Herrmann, Dormagen, all of Germany

[73] Assignee: Bayer Aktiengesellschaft, Leverkusen, Germany

[21] Appl. No.: 692,680

[22] Filed: Aug. 6, 1996

Related U.S. Application Data

[63] Continuation of Ser. No. 392,437, Feb. 22, 1995, abandoned.

[30] Foreign Application Priority Data

Mar. 1, 1994 [DE] Germany .......................... 44 06 630.9

[51] Int. Cl.$^6$ .......................... C09B 67/02; D06P 1/613; D06P 1/651
[52] U.S. Cl. .......................... 8/506; 8/526; 8/552; 8/576; 8/582; 252/384; 424/501
[58] Field of Search .......................... 8/524, 552, 576, 8/582; 252/384; 424/501

[56] References Cited

U.S. PATENT DOCUMENTS

| | | |
|---|---|---|
| 2,486,562 | 11/1949 | Iamarino et al. |
| 2,604,649 | 7/1952 | Stephensen et al. |
| 4,137,398 | 1/1979 | Muzzio ........................ 536/4 |
| 4,238,577 | 12/1980 | Arendt . |
| 4,275,244 | 6/1981 | Helfert et al. ........................ 568/624 |
| 4,436,522 | 3/1984 | Niwa et al. ........................ 8/524 |
| 4,562,096 | 12/1985 | Lo et al. . |
| 4,722,736 | 2/1988 | Hull ........................ 8/524 |
| 5,366,512 | 11/1994 | Mischke et al. . |
| 5,424,359 | 6/1995 | Arashiro et al. ........................ 525/64 |

FOREIGN PATENT DOCUMENTS

| | | |
|---|---|---|
| 0023638 | 2/1981 | European Pat. Off. . |
| 0067022 | 12/1982 | European Pat. Off. . |
| 200388 | 5/1986 | European Pat. Off. . |
| 0200388 | 11/1986 | European Pat. Off. . |
| 842791 | 7/1960 | United Kingdom . |
| 1587210 | 4/1981 | United Kingdom . |

OTHER PUBLICATIONS

Derwent Abstract, abstracts of JP 56–24, 141 (Jul. 1981).

*Primary Examiner*—Margaret Einsmann
*Attorney, Agent, or Firm*—Sprung Kramer Schaefer & Briscoe

[57] ABSTRACT

To prevent dusting of a solid such as a crop protection agent, a pharmaceutical or a dyestuff, there is added thereto as a dustproofing agent a compound of the formula I $$R_1 + A + Z + B + R_2, \quad (I)$$

in which
Z represents $Z_1$ or $Z_2$ where
$Z_1$ denotes a bivalent radical of the formula $$-O-\overset{\overset{\displaystyle O}{\|}}{C}-W-\overset{\overset{\displaystyle O}{\|}}{C}-O-$$

in which
W represents a direct bond or a $C_1$–$C_3$ unit, and
$Z_2$ represents unsubstituted arylenedioxy, wherein the remaining variables are defined herein.

5 Claims, No Drawings

DUSTPROOFING AGENTS

This application is a continuation of application Ser. No. 08/392,437, filed Feb. 22, 1995 now abandoned.

The invention relates to novel dustproofing agents and solid preparations containing them.

Solid, in particular pulverulent, dyestuff preparations have the tendency to dust during handling and during filling processes or transfers to other containers and when used for preparing dyeing liquors or dyestuff printing pastes. Depending on the particle fineness and the residual moisture content, they exhibit more or less pronounced dusting. In order to avoid losses of product and contamination of the workplace and especially in order to ensure work hygiene for the operating staff, these powders are in general treated with dustproofing auxiliaries, such as mineral oils, alone or in combination with anionic or non-ionic surfactants, phthalic esters, silicones or alkanediols (cf., for example, DE-A 1,117,582, U.S. Pat. No. 2,604,649, DE-A 834,237, DE-A 4,035,029). In order to obtain low-dusting preparations, the dust-proofing additives mentioned must be admixed to the dyestuff in amounts of about 2–10%. However, using these known products has certain disadvantages. Thus, for example, mineral oils promote agglomeration of the dyestuff powder. Furthermore these agents result in deterioration of the redispersing and dissolving properties, such as, for example, the cold-water solubility which is important for the cold-dyeing method. Furthermore, the addition of mineral oils frequently leads to the formation of oily deposits in the dyeing liquors, as a result of which specky dyeings and contaminations of the dyeing machines are obtained. While this is counter-acted by the addition of surfactants, it nevertheless results in troublesome foaming and moreover is unsuccessful in the presence of electrolytes in the dyeing bath.

The disadvantages of the silicones are, for example, apart from demixing of the dyeing liquors, speck formation on the dyed material and deposits on the edges in the dyeing apparatuses.

A disadvantage of the alkanediols is, for example, their limited effectiveness.

Since dusting substances in general may be the source of a health risk to the persons handling them, high demands are nowadays made on the low-dusting characteristics of solid materials, for example dyestuffs. A frequently used method for determining the dusting behaviour of dyestuffs is described, for example, in "Textilveredlung", 24 (1989), p. 277–290. In this method, a definite amount of dyestuff powder is suddenly dropped through a downpipe to the bottom of an air-tight dust-producing apparatus. After 5 seconds, the dust formed is sucked off by applying a vacuum and collected on a filter. The filter is rated visually by comparison with the 5-step grey scale of ISO 105-A03. A dust value of 1 means that the product is high-dusting, and a dust value of 5 that no dust deposit can be detected on the filter. Today's requirements demand that low-dusting dyestuff preparations exhibit dust values of at least 3. For toxic products, it is strongly recommended to aim for values of >4.

DE-A-2,656,406 and EP-A-200,388 have already tried to solve this problem by means of condensation products of aryl hydroxides and ethylene oxide. However, such dust-binding agents still exhibit a number of disadvantages which the present application needs to improve.

Low-dusting and dust-free solid preparations, in particular dyestuff preparations containing, in addition to the solid, a compound of the formula (I)

in which

Z represents $Z_1$ or $Z_2$ where $Z_1$ denotes a bivalent radical of the formula

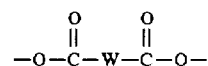

in which

W represents a direct bond or a $C_1$–$C_3$ unit, in particular —$CH_2$—, —$CH_2CH_2$—, trans-(—CH=CH—) or cis-(—CH=CH—) and $Z_2$ represents unsubstituted arylenedioxy or aryleneoxy, in particular phenylenedioxy or phenyleneoxy, A and B each denote, independently of one another, a bivalent radical consisting of up to 50 ethylene oxide units and/or up to 50 propylene oxide units arranged randomly or in blocks, or represent a direct bond where the alkyleneoxy groups are oriented in such a manner that the terminal oxygen atom of A is attached to $R_1$, and that of B is attached to $R_2$, with the proviso that in each case only one of the bivalent radicals A or B may adopt the meaning of a direct bond and in the case where Z denotes $Z_2$ at least one of the two radicals A or B contains propylene oxide and ethylene oxide units, preferably in a ratio of 0.5:1 to 10:1, in particular 1:1 to 4:1, $R_1$ and $R_2$ denote, independently of one another, hydrogen or $C_1$–$C_4$-alkyl, in particular methyl, ethyl, n-propyl, iso-propyl, n-butyl and iso-butyl have now been found.

Preference is given to solid preparations containing, in addition to the solid, a compound of the formula (I) having the formula (II)

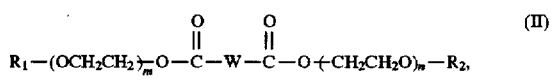

in which m and n represent, independently of one another, 0 to 10 and the sum of m and n is greater than zero, w represents a direct bond or denotes —$CH_2$—, —$CH_2CH_2$—, cis(—CH=CH—) or trans(—CH=CH—) and $R_1$ and $R_2$ denote, independently of one another, methyl, ethyl, n-propyl, iso-propyl, n-butyl or iso-butyl.

Compounds of the formula (II) can be prepared, for example, by esterifying or transesterifying the corresponding dicarboxylic acids, dicarboxylic esters or dicarboxylic anhydrides of oxalic acid, malonic acid, succinic acid, fumaric acid and maleic acid with alcohols of the formula

and/or alcohols of the formula $$R_2-(OCH_2CH_2)_n-OH$$

where $R_1$, $R_2$, m and n have the meaning given for the compound of the formula (II).

Furthermore, preference is given to solid preparations containing compounds of the formula (I) in which $R_1$ and $R_2$ denote hydrogen and Z represents a phenylenedioxy or phenyloxy radical.

Particular preference is given to solid preparations containing, in addition to the solid, compounds of the formula (I) having the formulae (III) and/or (IV)

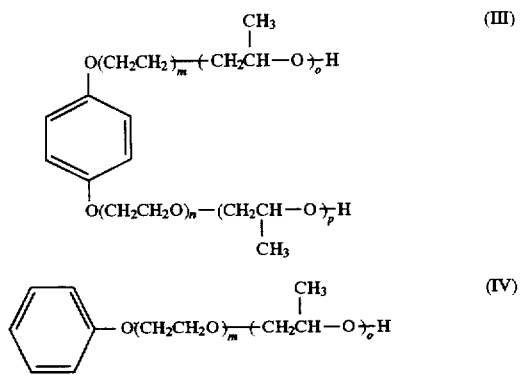

where m, n, o and p represent, independently of one another, 0 to 50 and the o/m ratio is 0.5:1 to 10:1, preferably 1:1 to 4:1.

The compounds of the formulae (III) and (IV) can be obtained, for example, by reacting the corresponding phenol compounds or hydroquinone compounds first with ethylene dioxide and then continuing the alkoxylation with propylene oxide. When this reaction is carried out in a high-boiling glycol ether (b.p. of about 150° C.) with potassium hydroxide catalysis, ethylene oxide and propylene oxide add to the above compound in succession in the desired ratio.

The indices of the alkylene oxide units m, n, o and p are statistical average values.

Very particular preference is given to those dustproofing agents of the formulae (III) and (IV) used according to the invention in which m represents 2 to 5, n represents 2 to 5, o represents 1 to 10 and p represents 1 to 10.

The invention also relates to dustproofing agents of the formula (I) such as defined above and to the preferred embodiments such as have already been described above for use in the solid preparations according to the invention.

Examples of solids present in the solid preparations containing the compounds of the formula (I) used according to the invention as dustproofing agents are crop protection agents, pharmaceuticals, but in particular dyestuffs. Examples of suitable dyestuffs are direct dyestuffs, cationic dyestuffs, reactive dyestuffs or dispersion dyestuffs and optical brighteners, but in particular reactive dyestuffs and cationic dyestuffs.

The solid preparations, in particular dyestuff preparations, generally contain, in addition to the solid, 0.001 to 10% by weight, relative to the overall preparation, of the compound of the formula (I) as dustproofing agent. Although a higher proportion of dustproofing agent is possible, it usually offers no advantage.

The solid preparations according to the invention usually have the following composition (relative to the overall preparation):

20 to 90% by weight, preferably 20 to 80% by weight, of solid, 0.001 to 10% by weight, preferably 0.5 to 6% by weight, in particular 0.5 to 3% by weight, of the compound of the formula (I).

In addition, the dyestuff preparations can contain customary additives in the usual amount. These can be, for example, standardizing agents, salts, residual water, buffers, wetting agents, dispersants, surfactants, binders or others.

Examples of customary and advantageous additives for reactive dyestuffs include: condensation products obtained from naphthalene, formaldehyde and sulphuric acid or from ditolyl ether, formaldehyde and $Na(HSO_3)$, $Na_2SO_4$, buffers and hydrotropic substances.

Examples of customary additives for disperse dyestuffs include: dispersing agents based on lignosulphonic acid, condensation products such as those used in reactive mixtures and wetting agents.

Examples of customary additives for direct dyestuffs include: inorganic salts, water-soluble starch products or water-softening agents.

Examples of customary additives for cationic dyestuffs include: inorganic salts, water-soluble and -insoluble starch products, inorganic acids, complexing agents.

The low-dusting dyestuff preparations can be prepared in various ways. Thus, for example, the dustproofing agent can be added to a dyestuff slurry (solution or dispersion), and the resulting mixture can then be converted into the dust-free powder or granule form under drying conditions, such as, for example, by spray-drying, fluidized-bed drying or drying and granulating. A further treatment of the dyestuff slurry before, during or after addition of the dustproofing agent is of course also possible. Thus, for example, prior to the addition of dustproofing agent, reactive dyestuffs can be desalted using the membrane technology. A further treatment can also consist in providing the slurry with further additives, such as standardizing agents, salts, buffers and the like.

Starting from solid dyestuffs, such as powders or granules, addition of the dustproofing agent can take place in powder blends, for example in the form of an aqueous emulsion or as an aerosol. Furthermore, the dustproofing agent can be added in the form of a spray mist in a fluidized-bed drier or else after spray drying. Thus, for example, granules obtained by the roller, mixing or spray granulation methods which are subject to abrasion and thus give rise to dust formation can be made low-dusting or dust-free by the method mentioned, in particular by mixing the dustproofing agent.

The preparations according to the invention, in particular those of water-soluble or water-dispersible dyestuffs, are distinguished in particular by very good dust values ($\geq 4$) and in addition possess further desirable properties, such as very good storage stabilities of 4 weeks even at 50° C. The preparations according to the invention retain their solubility or their solution stability in aqueous solution or electrolyte solution. The examples which follow illustrate the dustproofing properties. The dustproofing agents used therein have no adverse effect whatsoever on the solubility of the dyestuff, for example in aqueous solution or when electrolytes such as $Na_2SO_4$, NaCl or $Na_2CO_3$ are added.

EXAMPLE 1

In a mixing apparatus, 98 g of an electrolyte-containing granular dyestuff of the formula

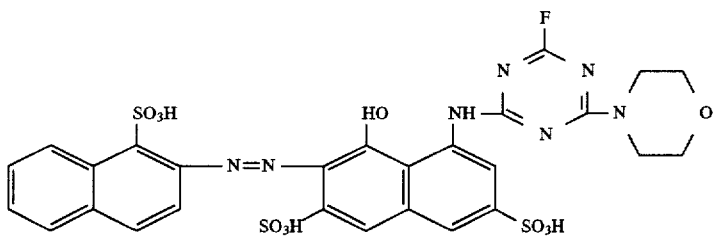

having a dyestuff content of 70% by weight are mixed in the form of the alkali metal salt with 2 g of the compound of the formula

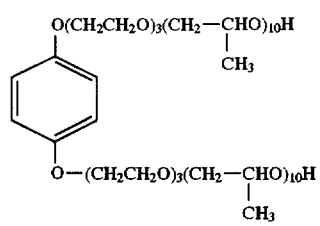

obtained by reacting hydroquinone first with 6 mol equivalent of ethylene oxide and then with 20 mol equivalent of propylene oxide until a homogeneous mixture is obtained. The indices of the alkylene oxide units given in the formula are idealized values. The dyestuff preparation obtained has a dust value of 4–5.

The advantageous property of the dyestuff preparation according to the invention of showing only very little dusting remains unchanged even during 4 weeks of storage at 50° C.

The dyestuff preparation is used for dyeing cellulose fibre materials, such as cotton, the good quality of the dyeing not being adversely affected by the dustproofing agent used according to the invention.

EXAMPLE 2

98 g of the granular starting dyestuff used in Example 1 are mixed with 2 g of the compound of the formula

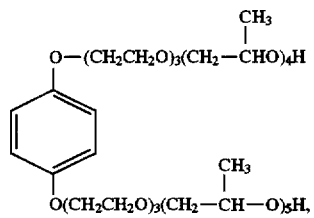

obtained by reacting phenol first with 5 mol equivalent of ethylene oxide and then with 10 mol equivalent of propylene oxide in a mixing apparatus until a homogeneous mixture is obtained. The indices of the alkylene oxide units in the above formula are understood as meaning idealized values. The resulting dyestuff preparation according to the invention has a dust value of 4 which remains unchanged even after 4 weeks of storage at 50° C.

The dyestuff preparation is used for dyeing cellulose fibre materials, such as cotton, the good quality of the dyeings and prints not being adversely affected at all by the dustproofing agent used according to the invention.

EXAMPLE 3

In a mixing apparatus, 98 g of an electrolyte-containing granular dyestuff of the formula

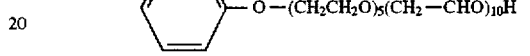

having a dyestuff content of 83% by weight are mixed in the form of the alkali metal salt with 2 g of the compound of the formula

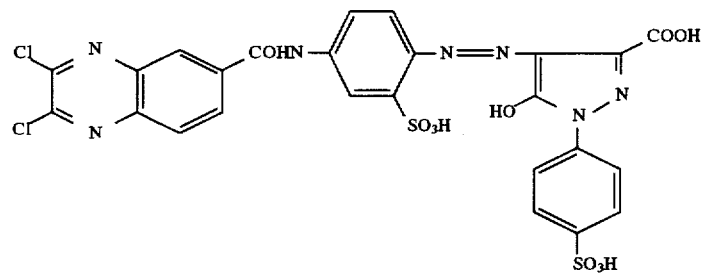

obtained by reacting hydroquinone first with 6 mol equivalent of ethylene oxide and then with 9 mol equivalent lent of propylene oxide until a homogeneous mixture is obtained.

The indices of the alkylene oxide units in the above formula are understood as meaning idealized values.

The resulting dyestuff preparation is readily soluble and exhibits a dust value of 5. This advantageous property of the dyestuff preparation according to the invention of showing only very little dusting remains unchanged even after 4 weeks of storage at 50°C.

The dyestuff preparation is used for dyeing cotton in strong level shades, the good quality of the dyeings and prints not being adversely affected at all by the dustproofing agent used according to the invention.

EXAMPLE 4

The dyestuff preparation of this example is prepared by the method of Example 3, except that the dustproofing agent used there is replaced by the same amount (2 g) of bis (methylglycol) maleate of the formula

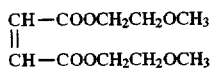

The dyestuff preparation thus obtained is readily water-soluble and has a dust value of 5 which remains unchanged even after storing the preparation at 50° C. for 4 weeks.

EXAMPLE 5

A dyestuff preparation is prepared by the method of Example 3 using the dyestuff of Example 3 but replacing the dustproofing agent used there by 2 g of methylglycol ethylglycol maleate of the formula

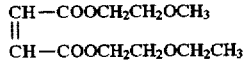

The dyestuff preparation thus obtained is highly water-soluble and has a dust value of 4 to 5 which remains unchanged even after 4 weeks of storage at 50° C. The dyeings and prints obtained from cotton are of the same high quality as those from Example 3.

EXAMPLE 6

47 g of a dyestuff powder of the formula

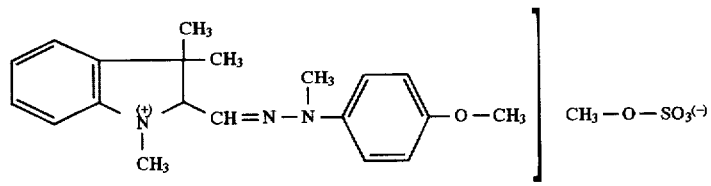

are milled together with 52 g of sodium sulphate and 1 g of methylglycol ethylglycol maleate of the formula

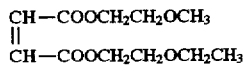

and mixed until a homogeneous mixture is obtained. This gives a readily water-soluble dyestuff preparation efficiently freed from dust. The dyestuff mixture according to the invention remains unchanged even after being stored for over 4 weeks not only at room temperature but also at a storage temperature of 50° C.

EXAMPLE 7

47 g of a dyestuff powder from Example 6 are mixed with 52 g of sodium sulphate and 1 g of bis(methylglycol) maleate of the formula

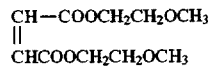

until a homogeneous mixture is obtained. The resulting dyestuff preparation has been efficiently freed from dust and exhibits a dust value which remains stable even after 4 weeks of storage at room temperature and at 50° C. The dustproofing agents used according to the invention in Examples 6 and 7 have no adverse effect on the water solubility and the dyeing in polyacrylonitrile fibres. Oil/emulsifier mixtures used for comparison gave poorer dust performance when used identically.

EXAMPLE 8

76 g of the powder dyestuff of the formula

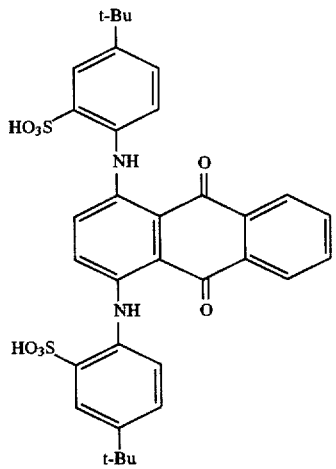

are intimately mixed with 20 g of dextrin and 4 g of methylglycol butylglycol maleate of the formula

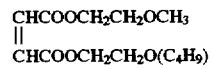

to give a low-dusting dyestuff mixture which is readily water-soluble. The dyestuff mixture freed from dust according to the invention shows unchanged dust values after 4 weeks of storage at room temperature and also at 50° C.

EXAMPLE 9

76 g of a dyestuff powder from Example 8 are mixed with 20 g of dextrin and 4 g of methylglycol ethylglycol maleate of the formula

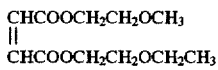

in a mixing apparatus until a homogeneous mixture is obtained.

The resulting dyestuff preparation is readily water-soluble, low-dusting and exhibits stable dust values even after 4 weeks of storage at 50° C. Oil/emulsifier mixtures used for comparison gave considerably poor dust values when used identically.

EXAMPLE 10

96 g of a spray-dried dyestuff containing 49.2% of the commercially available sodium salt of a naphthalene-sulphonic acid/formaldehyde condensation product, 8% of residual moisture content and 42.8% of the dyestuff of the formula

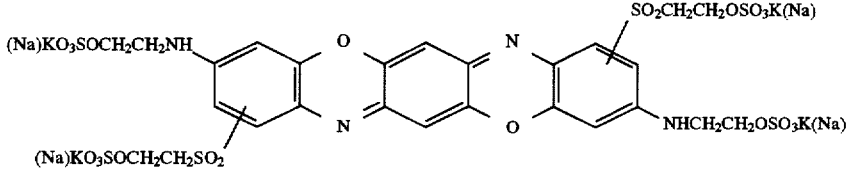

are mixed with 4 g of methylglycol butylglycol maleate of the formula

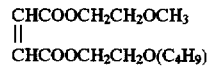

until a homogeneous mixture is obtained. This gives a dyestuff mixture which has been very efficiently freed from dust and remains dust-free even after 4 weeks of storage at 60° C. The application properties of this dyestuff preparation freed from dust (solubility, dyeing on cellulose fibres) remain unchanged.

EXAMPLE 11

In a mixing apparatus, 99 g of the standardized reactive dyestuff (containing 57% of dyestuff, 4.5% of buffer, 29% of a condensation product obtained from naphthalene, formaldehyde and sulphuric acid and 8% of residual moisture content) of the formula

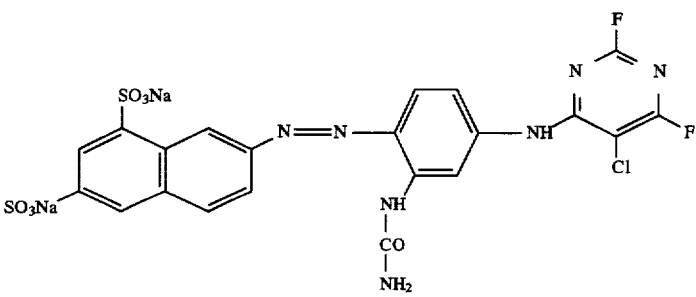

and 1 g of the dustproofing compound

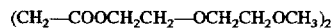

are mixed to give a preparation freed from dust, which preparation has a dust value around 5 and good water solubility and does not give any deposits on the edges in a padding liquor.

When mixed with mineral oil, the same reactive dyestuff gives only moderate dust values in conjunction with the above deposits in the dyeing liquor.

We claim:

1. A solid crop protection preparation, pharmaceutical preparation or a dyestuff preparation, in the form of a powder or granules, comprising 20–90% by weight of a solid crop protection agent, pharmaceutical composition or dyestuff, and 0.001 to 10% by weight of a compound of the formula (I)

$$R_1 + A + Z + B + R_2, \quad (I)$$

in which

Z represents $Z_1$ or $Z_2$ where $Z_1$ denotes a bivalent radical of the formula

in which

W represents a direct bond or a $C_1$–$C_3$ unit and $Z_2$ represents unsubstituted phenylenedioxy A and B each denote independently of one another a direct bond or a bivalent radical selected from the group consisting of up to 50 ethylene oxide units, up to 50 propylene oxide units or mixed units of up to 50 ethylene oxide units and up to 50 propylene oxide units which are arranged randomly or in blocks, where the foregoing ethylene oxide units propylene oxide units or mixed units of ethylene oxide and propylene oxide are oriented in such a manner that the terminal oxygen atom of A is attached to $R_1$ and that of B is attached to $R_2$, with the proviso that in each case only one of the bivalent radicals A or B may adopt the meaning or a direct bond and in the case where Z denotes $Z_2$ at least one of the two radicals A and B contains propylene oxide and ethylene oxide units, $R_1$ and $R_2$ denote, independently of one another hydrogen or $C_1$-$C_4$-alkyl.

2. A solid preparation according to claim 1 wherein the compound of the formula I is represented by formula (II)

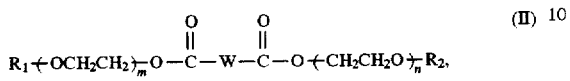

in which m and n represent, independently of one another, 0 to 10 and the sum of m and n is greater than zero, W represents a direct bond or —$CH_2$—, —$CH_2CH_2$—, cis (—CH=CH—) or trans (—CH=CH—) and $R_1$ and $R_2$ denote, independently of one another, methyl, ethyl, n-propyl, iso-propyl, n-butyl or iso-butyl.

3. Solid preparation according to claim 1 in which $R_1$ and $R_2$ of the formula (I) denote hydrogen, and Z represents an unsubstituted phenylenedioxy radical.

4. Solid preparation according to claim 1, wherein the compound of formula I is represented by formula (III)

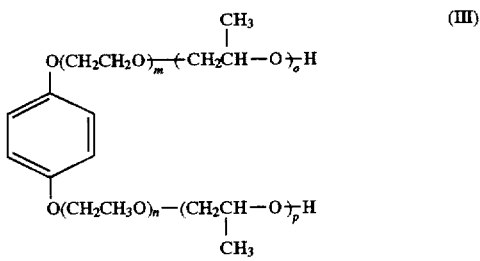

wherein n and p represent, independently of one another, 0 to 50
m represents 2–50, o represents 1–50 and the o/m ratio is 0.5 to 10:1.

5. A solid preparation according to claim 1, comprising 20–90% by weight of a dyestuff and 0.001 to 10% by weight of a compound of the formula (I).

* * * * *

UNITED STATES PATENT AND TRADEMARK OFFICE
CERTIFICATE OF CORRECTION

PATENT NO. : 5,762,651
DATED : June 9, 1998
INVENTOR(S) : Horst Brandt, et al.

It is certified that error appears in the above-indentified patent and that said Letters Patent is hereby corrected as shown below:

| | |
|---|---|
| Col. 11, Line 2 | Delete "or" and substitute --of-- |
| Col. 12, Line 5 | Delete \\ // |

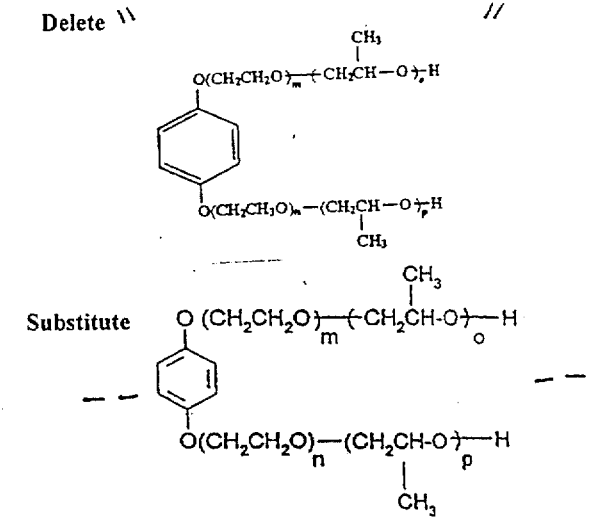

Substitute

Signed and Sealed this

Twenty-third Day of November, 1999

Attest:

Q. TODD DICKINSON

*Attesting Officer*  *Acting Commissioner of Patents and Trademarks*

UNITED STATES PATENT AND TRADEMARK OFFICE
CERTIFICATE OF CORRECTION

PATENT : 5,762,651

DATED : June 9, 1998

INVENTOR(S) : Horst Brandt, et al.

It is certified that error appears in the above-identified patent and that said Letters Patent is hereby corrected as shown below:

On the title page item [56] References Cited, Other Publications:

Delete " Derwent Abstract, abstracts of JP 56-24,141 (Jul. 1981)."

Signed and Sealed this

Twenty-third Day of May, 2000

*Attest:*

Q. TODD DICKINSON

*Attesting Officer*        *Director of Patents and Trademarks*